United States Patent
Seeba et al.

(10) Patent No.: US 9,670,135 B2
(45) Date of Patent: Jun. 6, 2017

(54) PREPARATION OF HALOGENATED DI-SUBSTITUTED BENZYLAMINES, PARTICULARLY HALOGENATED DIALKYLBENZYLAMINES

(71) Applicant: BAYER CROPSCIENCE AKTIENGESELLSCHAFT, Monheim am Rhein (DE)

(72) Inventors: Johann Seeba, Leverkusen (DE); Günter Schlegel, Leverkusen (DE); Martin Littmann, Leverkusen (DE); Rafael Warsitz, Essen (DE); Mark James Ford, Wiesbaden-Breckenheim (DE)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 0 days.

(21) Appl. No.: 15/103,110

(22) PCT Filed: Dec. 8, 2014

(86) PCT No.: PCT/EP2014/076822
§ 371 (c)(1),
(2) Date: Jun. 9, 2016

(87) PCT Pub. No.: WO2015/086490
PCT Pub. Date: Jun. 18, 2015

(65) Prior Publication Data
US 2016/0304435 A1    Oct. 20, 2016

(30) Foreign Application Priority Data
Dec. 11, 2013    (EP) ..................................... 13196718

(51) Int. Cl.
| | |
|---|---|
| *C07C 209/08* | (2006.01) |
| *C07C 209/04* | (2006.01) |
| *C07C 209/84* | (2006.01) |
| *C07C 209/14* | (2006.01) |

(52) U.S. Cl.
CPC .......... *C07C 209/08* (2013.01); *C07C 209/04* (2013.01); *C07C 209/84* (2013.01); *C07C 209/14* (2013.01)

(58) Field of Classification Search
None
See application file for complete search history.

(56) References Cited

U.S. PATENT DOCUMENTS

| | | |
|---|---|---|
| 3,646,147 A | 2/1972 | Dadekian |
| 2007/0073086 A1 | 3/2007 | Mathiaparanam |

FOREIGN PATENT DOCUMENTS

| | | |
|---|---|---|
| EP | 0 034 425 A2 | 8/1981 |
| WO | 2008125592 A1 | 10/2008 |
| WO | 2012139561 A1 | 10/2012 |
| WO | 2013017611 A1 | 2/2013 |

OTHER PUBLICATIONS

International Search Report dated Feb. 12, 2015, issued in PCT/EP2014/076822.

*Primary Examiner* — Clinton Brooks
(74) *Attorney, Agent, or Firm* — McBee Moore Woodward Vanik IP LLC

(57) ABSTRACT

The present invention relates to a novel process for preparing halogenated di-substituted benzylamines, particularly halogenated dialkylbenzylamines.

20 Claims, No Drawings

PREPARATION OF HALOGENATED DI-SUBSTITUTED BENZYLAMINES, PARTICULARLY HALOGENATED DIALKYLBENZYLAMINES

CROSS REFERENCE TO RELATED APPLICATIONS

This application is a §371 National Stage Application of PCT/EP2014/076822, filed 8 Dec. 2014, which claims priority to EP 13196718.4, filed 11 Dec. 2013.

BACKGROUND

Field of the Invention

The present invention relates to a novel process for preparing halogenated di-substituted benzylamines, particularly halogenated dialkylbenzylamines.

Description of Related Art

The preparation of halogenated dialkylbenzylamines is known from the prior art. For example, WO 2012/139561 A1 describes a process for preparing aromatic or heteroaromatic amines from the corresponding aryl and heteroaryl halides or sulphonates in the presence of a catalyst and a base.

US 2007/0073086 A1 describes a process for preparing diphenylamines wherein aryl halides are reacted with aromatic amines in the presence of an organic solvent, alkali metal hydroxide and a phase-transfer catalyst.

Similarly U.S. Pat. No. 3,646,147 P describes a process for preparing tertiary amines wherein alkyl chlorides are reacted with primary amines in the presence of alkali metal iodides as catalysts.

WO 2008/125592 A1 likewise discloses a process for preparing o-chloromethylphenylglyoxylic esters. This document describes the synthesis of 2-chlorobenzylmorpholine wherein morpholine is added to a solution of 2-chlorobenzyl chloride in toluene and 15% strength aqueous sodium hydroxide solution.

EP 0 034 425 A1 describes a process for preparing tertiary amines wherein starting from a mono- or di-secondary amine said amine is arylated via an Ullmann condensation with a di-iodoaryl compound in the presence of a copper catalyst.

WO 2013/017611 A1 likewise discloses a process for preparing N,N-dialkylbenzylamines. This process comprises reacting dimethylamine and 2-chlorobenzyl chloride in a molar ratio of 3:1 or greater.

Disadvantages of the processes described in the prior art include the use of costly catalysts or the use of a large excess of secondary amines which entails costly and inconvenient removal of the amine.

The problem addressed by the present invention was therefore that of providing a novel process for preparing halogenated di-substituted benzylamines, particularly halogenated dialkylbenzylamines, wherein the use of catalysts is not necessary, the reaction mixture does not comprise an excess of the secondary amine and yet the end product is obtainable in high purity and yield.

SUMMARY

It has now been found, surprisingly, that despite a lower molar ratio between benzyl halide and di-substituted amine, particularly dialkylamine, the process according to the invention gives yields of not less than 95% and a purity for the end product of 99%. Said process moreover dispenses with recovery of the amine.

The present invention provides a process for preparing compounds of formula (I)

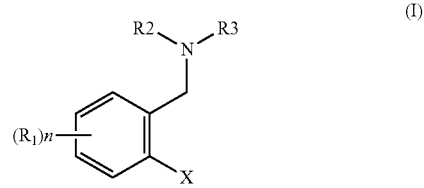

where
$R_1$ is hydrogen, $C_1$-$C_8$-alkyl, $C_2$-$C_6$-alkenyl, $C_3$-$C_6$-cycloalkyl, $C_1$-$C_8$-alkoxy, $C_1$-$C_6$-alkoxy-$C_2$-$C_6$-alkenyl, phenyl, benzyl, preferably hydrogen;
$R_2$, $R_3$ are each independently $C_1$-$C_8$-alkyl, aryl, heteroaryl, $C_2$-$C_6$-alkenyl, $C_3$-$C_8$-cycloalkyl, $C_1$-$C_6$-alkoxy, $C_1$-$C_6$-haloalkyl, $C_1$-$C_6$-haloalkoxy, preferably $C_1$-$C_6$-alkyl, more preferably methyl, ethyl, n-propyl, n-butyl, most preferably methyl or ethyl,
X is chlorine or bromine, preferably chlorine and
n is 0, 1, 2, 3 or 4, preferably 0;
characterized in that it comprises initially charging as reaction medium an alkali metal hydroxide in a concentration of from 20% to 50%, preferably from 25% to 45%, more preferably from 30% to 40%, subsequently reacting in a first step A) the compounds (II) and (III)

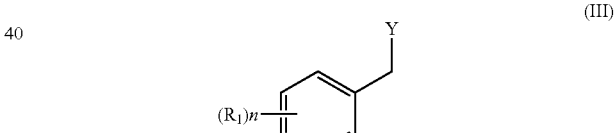

where
$R_1$, $R_2$, $R_3$ and X are as defined above and
Y is chlorine, bromine, iodine, an alkylsulphonate (—$OSO_2$-alkyl, preferably —$OSO_2CH_3$, —$OSO_2CF_3$) or an arylsulphonate (—$OSO_2$-aryl, preferably —$OSO_2Ph$, —$OSO_2PhMe$), preferably chlorine or bromine, more preferably chlorine;
in a molar ratio of from 0.9 to 2.5, preferably 1 to 2, more preferably 1.1 to 1.3, and adding to the reaction mixture in a second step B) from 0 to 9 mol of water, preferably from 1 to 5 mol, more preferably from 1 to 3 mol, based on 1 mol of the compound of formula (III), and subsequently removing the aqueous phase from the product.

DETAILED DESCRIPTION OF A PREFERRED EMBODIMENT

It is generally preferable to carry out step A) in the absence of an organic solvent. It is particularly preferable to carry out both of steps A) and B) of the process according to the invention in the absence of an organic solvent.

The reaction temperature of the process according to the invention is between −20° C. and 70° C., preferably between 0° C. and 65° C., more preferably between 20° C. and 60° C.

The process according to the invention can be carried out at a reaction pressure of from 0.1 bar to 32 bar, preferably at 0.5 to 10 bar, more preferably at 0.9 bar to 1.5 bar.

It is very particularly preferred when the compound of formula (I) is 2-chloro-N,N-dimethylbenzylamine.

It is very particularly preferred when the compound of formula (II) employed is dimethylamine, preferably as a 35% to 45% strength aqueous solution, more preferably as a 40% strength aqueous solution.

It is very particularly preferred when the compound of formula (III) is 2-chlorobenzyl chloride.

Useful alkali metal hydroxides are potassium hydroxide or sodium hydroxide, sodium hydroxide being preferred.

It is preferable when step A) of the process according to the invention comprises adding the compounds of formulae (II) and (III) to the initially charged aqueous sodium hydroxide solution over 0.2 to 6 h. It is likewise possible and likewise preferable to initially add the compounds of formula (II) to the aqueous sodium hydroxide solution and subsequently meter compounds of formula (III) into the resulting mixture.

It is also possible for step A) to comprise initially charging compound of formula (III) and aqueous sodium hydroxide solution and adding compound of formula (II) to the resulting mixture.

It is preferable when on completion of the addition of the compounds of formulae (II) and (III) in step A) of the process according to the invention the mixture is post-reacted for 1 to 24 h, preferably 4 to 18 h, more preferably 6 to 12 h.

If necessary, the addition of water in step B) of the process according to the invention can be followed by a purification step C). This comprises adding to the reaction mixture an organic solvent in a molar ratio of solvent to crude product of from 1:1 to 1:50, preferably from 1:5 to 1:20, more preferably from 1:5 to 1:10. It is particularly preferable when this comprises adjusting the pH of the reaction medium to a value (RT) between 0 and 2 by addition of mineral acid, preferably hydrochloric acid or sulphuric acid, more preferably hydrochloric acid. This is followed by removal of the organic phase, wherein the aqueous phase is admixed with an organic solvent and the molar ratio between solvent and crude product is from 10:1 to 1:50, preferably from 5:1 to 1:10, more preferably from 2:1 to 1:2. Here, the pH is adjusted to a value (RT) between 11 and 14 by addition of a base, preferably aqueous sodium hydroxide solution. The aqueous phase is subsequently removed.

One preferred embodiment of the process according to the invention comprises the purification step C).

A further step D) comprises removing the organic solvent from the product, preferably by means of distillation. When step C) has been omitted an organic solvent can be used for step D), said solvent being removed again in the distillation. The distillation in the process according to the invention serves solely to remove residual water, any residual amounts of organic solvent and residual amounts of the compound of formula (II). The compound (I) itself is not distilled off. Said compound (I) is obtained in high purity once step D) has been carried out.

It is preferable when the process according to the invention comprises the steps A), B) and D). It is particularly preferable when it comprises the steps A), B), C) and D).

Useful organic solvents include apolar solvents, for example toluene, methylcyclohexane or methyl-tert-butyl ether. Toluene is preferred.

The process according to the invention can be carried out both batchwise and continuously, the batchwise procedure being preferred.

The continuous mode may be carried out using a tubular reactor for step A) for example. In accordance with the invention, sodium hydroxide is continuously passed through the tube and the compound of formula (II) is then admixed therewith using a nozzle or static mixer, for example. The metered addition is subsequently effected downstream of the compound of formula (III). The addition can also be effected at a plurality of points in the reactor via addition of sub-streams. A sufficient flow rate in the tubular reactor needs to be established here in order to achieve thorough commixing of the phases.

Step B) is subsequently effected as for the batch process or likewise in a continuous process. In the continuous process for step B) the water is continuously added at the downstream end of the tubular reactor. Here, the tubular reactor can optionally have a further tubular reactor connected downstream of it. The phase separation can be carried out with a continuous phase separator for example. Alternatively, the addition of water and the phase separation can be effected in a mixer-settler apparatus.

This can be followed by step C). This can once more be effected batchwise or may be done continuously with a plurality of mixer-settler apparatuses.

This can be followed by step D). Here too, the distillation can be carried out either batchwise or in the form of a continuous distillation.

It is likewise possible and preferable to carry out the process according to the invention in a continuous mode in a stirred-tank cascade. Here, the aqueous sodium hydroxide solution and the compound of formula (II) are commixed in a stirred tank and the mixture is continuously transferred into a second stirred tank. The compound of formula (III) is continuously admixed into said mixture in the second stirred tank. This mixture is subsequently passed through further stirred tanks in order to complete the reaction. It is possible to use 1 to n serially connected stirred tanks where n is 20. n is preferably 1 to 10, more preferably 1 to 3. It is also possible to continuously commix the aqueous sodium hydroxide solution and the compounds of formulae (II) and (III) with the aqueous sodium hydroxide solution together in the first stirred tank and subsequently transfer the mixture into 1 to n further stirred tanks.

The mixture is subsequently worked-up in step B) as described hereinabove either batchwise or continuously. Steps C) and D) or either of the two steps can be repeated. These steps can be carried out as described hereinabove either continuously or batchwise.

The high purity of the compounds of formula (I) obtainable by the process according to the invention makes it possible to use said compounds in metallation reactions, for example Grignard reactions, directly and without further purification.

The definitions of the symbols given in the above formulae comprise collective terms which generally represent the following substituents:

Alkyl: saturated, straight-chain or branched hydrocarbon radicals having 1 to 8, preferably 1 to 6 and more preferably 1 to 3, carbon atoms, for example $C_1$-$C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl. This definition also applies to alkyl as part of a composite substituent, for example cycloalkylalkyl, hydroxyalkyl etc., unless defined elsewhere, for example alkylthio, alkylsulphinyl, alkylsulphonyl, haloalkyl or haloalkylthio. When the alkyl is at the end of a composite substituent as in alkylcycloalkyl for example, the part of the composite substituent at the start, for example the cycloalkyl, may be mono- or polysubstituted identically or differently and independently by alkyl. The same also applies to composite substituents in which other radicals, for example alkenyl, alkynyl, hydroxyl, halogen, formyl etc., are at the end.

Alkenyl: unsaturated, straight-chain or branched hydrocarbon radicals having 2 to 6 carbon atoms and a double-bond in any position, for example $C_2$-$C_6$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl. This definition also applies to alkenyl as part of a composite substituent, for example haloalkenyl etc., unless defined elsewhere;

Alkoxy: saturated, straight-chain or branched alkyloxy, alkenyloxy or alkynyloxy radicals having 1 to 6 and preferably 1 to 3 carbon atoms, for example $C_1$-$C_6$-alkoxy such as methoxy, ethoxy, propoxy, 1-methylethoxy, butoxy, 1-methylpropoxy, 2-methylpropoxy, 1,1-dimethylethoxy, pentoxy, 1-methylbutoxy, 2-methylbutoxy, 3-methylbutoxy, 2,2-dimethylpropoxy, 1-ethylpropoxy, hexoxy, 1,1-dimethylpropoxy, 1,2-dimethylpropoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy or $C_1$-$C_6$-alkenyloxy such as but-3-en-1-yloxy and allyloxy or $C_1$-$C_6$-alkynyloxy such as prop-2-yn-1-yloxy, but-2-yn-1-yloxy, pent-2-yn-1-yloxy, but-3-yn-1-yloxy. This definition also applies to alkoxy as part of a composite substituent, for example haloalkoxy, alkynylalkoxy etc., unless defined elsewhere;

Cycloalkyl: monocyclic, saturated hydrocarbyl groups having 3 to 8 and preferably 3 to 6 carbon ring members, for example (but not limited to) cyclopropyl, cyclopentyl and cyclohexyl; This definition also applies to cycloalkyl as part of a composite substituent, for example cycloalkylalkyl etc., unless defined elsewhere;

Haloalkyl: straight-chain or branched alkyl groups having 1 to 6 and preferably 1 to 3 carbon atoms (as specified hereinabove), where some or all of the hydrogen atoms in these groups may be replaced by halogen atoms as specified hereinabove, for example (but not limited to) $C_1$-$C_3$-haloalkyl such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2-difluoroethyl, 2,2-dichloro-2-fluoroethyl, 2,2,2-trichloroethyl, pentafluoroethyl and 1,1,1-trifluoroprop-2-yl. This definition also applies to haloalkyl as part of a composite substituent, for example haloalkylaminoalkyl etc., unless defined elsewhere;

Haloalkoxy: straight-chain or branched alkoxy groups having 1 to 6 and preferably 1 to 3 carbon atoms (as specified hereinabove) where some or all of the hydrogen atoms in these groups may be replaced by halogen atoms as specified hereinabove, for example (but not limited to) $C_1$-$C_3$-haloalkoxy such as chloromethoxy, bromomethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro-2-difluoroethoxy, 2,2-dichloro-2-fluoroethoxy, 2,2,2-trichloroethoxy, pentafluoroethoxy and 1,1,1-trifluoroprop-2-oxy. This definition also applies to haloalkoxy as part of a composite substituent, for example haloalkoxyalkyl etc., unless defined elsewhere;

Aryl: phenyl or naphthyl, preferably phenyl.

The process according to the invention is illustrated by the examples which follow, without being restricted thereto.

The abbreviation "eq" used hereinbelow is to be understood as meaning mole equivalents. Mole equivalents refers to the number of moles of the components in question divided by the number of moles of 2-chlorobenzyl chloride. Thus, 2-chlorobenzyl chloride is by definition always present in 1.0 mole equivalents.

EXAMPLE 1

Inventive Process

Step A) and Step B):

405.1 g of a 32% strength aqueous sodium hydroxide solution (1.07 eq) were initially charged and 469.3 g of a 35% strength solution of dimethylamine (1.2 eq) in water and 498.7 g of 2-chlorobenzyl chloride (1.0 eq) were metered concurrently into said aqueous sodium hydroxide solution over 1 hour at 40° C. The mixture was then stirred at 40° C. for a further 6 h. 85 g of water were added and the two liquid phases were then separated.

512.2 g of organic phase were obtained. Formula (I) compound content was 99.3%. The yield was 98.7%.

Step C)

512.2 g of the organic phase were stirred with 84.1 g of toluene and 557.9 g of 20% strength hydrochloric acid at 30° C. (pH 1) and the phases were subsequently separated. The organic phase was discarded. The aqueous phase was admixed with 603 g of toluene and 599.6 g of a 20% strength aqueous sodium hydroxide solution (pH 12). The phases were separated.

1104.6 g of organic phase were obtained. The yield was 99%.

Step D)

1104.6 g of organic phase were distilled at reduced pressure. 502.9 g of residue were obtained. The compound of formula (I) was obtained with a purity of 99% (HPLC) in a yield of 96.7%.

EXAMPLE 2

Process Comprising Steps A), B) and D) (i.e. No Purification after Step C))

Steps A) and B)

3996 g of a 32% strength aqueous sodium hydroxide solution (1.05 eq) were initially charged at −10° C. and 4125 g of a 40% strength solution of dimethylamine (1.2 eq) in water and 5005 g of 2-chlorobenzyl chloride (1.0 eq) were metered concurrently into said aqueous sodium hydroxide solution over 70 minutes. The temperature increased to +30° C. in the course of the metered addition. The mixture was then stirred at 40° C. for a further 12 h. 850 g of water were added and the two liquid phases were then separated.

5129.6 g of organic phase were obtained. Formula (I) compound content was 99.2% (HPLC). The yield was 98.4%.

Step D)

5129.6 g of organic phase were mixed with 849 g of toluene and distilled at reduced pressure. 5086 g of residue were obtained. The compound of formula (I) was obtained with a purity of 98.1% (HPLC) in a yield of 96.6%.

EXAMPLE 3

Process from WO 2008/125592 A1 with Morpholine 200 g of 2-chlorobenzyl chloride (1.0 eq) were initially charged and mixed with 346 g of toluene. 422 g of a 15% strength aqueous sodium hydroxide solution (1.3 eq) were added dropwise and 128.5 g of morpholine (1.2 eq) were then metered into the mixture. The mixture was heated to reflux and stirred at reflux overnight. The phases were then separated and the organic phase was washed with 200 g of water. The washed organic phase was dried by azeotropic distillation and some of the solvent was distilled off under vacuum. 271 g of 2-(morpholinomethyl)chlorobenzene were obtained. Compound purity: 90.9% (HPLC). Yield: 95.6%.

EXAMPLE 4

Process from WO 2008/125592 A1 with Morpholine without Addition of an Organic Diluent 32.9 g of 2-chlorobenzyl chloride (1.0 eq) were initially charged. 69.3 g of a 15% strength aqueous sodium hydroxide solution (1.3 eq) were added dropwise and 21.1 g of morpholine (1.2 eq) were then metered into the mixture. The mixture was heated to reflux and stirred at reflux overnight. The phases were then separated and the organic phase was washed with 32.2 g of water. The washed organic phase was dried by distillation under vacuum. 36.5 g of 2-(morpholinomethyl)chlorobenzene were obtained. Compound purity: 97.8% (HPLC), yield: 84.3%.

EXAMPLE 5

Process from WO 2008/125592 A1 Applied to Dimethylamine 32.9 g of 2-chlorobenzyl chloride (1.0 eq) were initially charged and diluted with 55.7 g of toluene. 23.1 g of a 45% strength aqueous sodium hydroxide solution (1.3 eq) were diluted with 30 g of water and added dropwise to the mixture of 2-chlorobenzyl chloride and toluene. 27.1 g of a 40% strength aqueous solution of dimethylamine (1.2 eq) were then metered into the mixture. Taking into account the water from the dimethylamine, a 15% strength aqueous sodium hydroxide solution is formed. The mixture was heated to reflux and stirred at reflux overnight. The phases were then separated and the organic phase was washed with 32.2 g of water. The washed organic phase was dried by azeotropic distillation under vacuum. This gave 33.6 g of a yellow oil. Purity of compound of formula (I): 81.3% (HPLC), yield: 80.5%.

The invention claimed is:

1. Process for preparing a compound of formula (I)

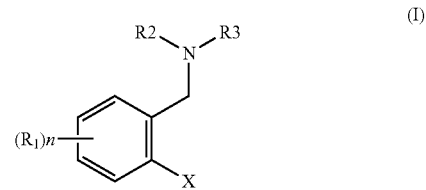

where

R$_1$ is hydrogen, C$_1$-C$_8$-alkyl, C$_2$-C$_6$-alkenyl, C$_3$-C$_6$-cycloalkyl, C$_1$-C$_8$-alkoxy, C$_1$-C$_6$-alkoxy-C$_2$-C$_6$-alkenyl, phenyl, or benzyl;

R$_2$, R$_3$ are each independently C$_1$-C$_8$-alkyl, aryl, heteroaryl, C$_2$-C$_6$-alkenyl, C$_3$-C$_8$-cycloalkyl, C$_1$-C$_6$-alkoxy, C$_1$-C$_6$-haloalkyl, or C$_1$-C$_6$-haloalkoxy;

X is chlorine or bromine, and n is 0, 1, 2, 3 or 4;

comprising initially charging as reaction medium an alkali metal hydroxide in a concentration of from 20% to 50% by weight, subsequently first A) reacting the compounds (II) and (III) in the reaction medium

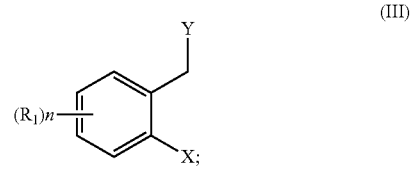

where
R₁, R₂, R₃ and X are as defined above and
Y is chlorine, bromine, iodine, an alkylsulphonate (—OSO₂-alkyl, preferably —OSO₂CH₃, —OSO₂CF₃) or an arylsulphonate (—OSO₂-aryl);
in a molar ratio of from 0.9 to 2.5 and
B adding to the reaction mixture in from 0 to 9 mol of water based on 1 mol of the compound of formula (III), and
subsequently removing the aqueous phase from the product.

2. Process according to claim 1, wherein A) is carried out in the absence of an organic solvent.

3. Process according to claim 1, wherein A) and B) are carried out in the absence of an organic solvent.

4. Process according to claim 1, wherein the reaction temperature is between −20° C. and 70° C.

5. Process according to claim 1, wherein the alkali metal hydroxide is sodium hydroxide.

6. Process according to claim 1, wherein on completion of the addition of the compounds of formulae (II) and (III) in A) the mixture is post-reacted for 1 to 24 h.

7. Process according to claim 1, wherein B) is followed by a purification C), wherein an organic solvent is added to the reaction mixture in a molar ratio of solvent to crude product of from 1:1 to 1:50.

8. Process according to claim 7, wherein the pH of the reaction medium is adjusted to a value (RT) between 0 and 2 by addition of mineral acid.

9. Process according to claim 7, comprising removing an organic phase, wherein an aqueous phase is admixed with an organic solvent and the molar ratio between solvent and crude product is from 10:1 to 1:50 and the pH is adjusted to a value (RT) between 11 and 14 with a base and the aqueous phase is removed.

10. Process according to claim 1, comprising D) distillative removal of residual water, any residual amounts of organic solvent and residual amounts of the compound of formula (II).

11. Process according to claim 10, comprising only A), B) and D).

12. Process according to claim 10, comprising A), B), C) and D) wherein C) comprises adding an organic solvent to the reaction mixture in a molar ration of solvent to crude product of from 1:1:50.

13. Process according to claim 1, wherein 1 to 5 mole of water are added in B).

14. Process according to claim 1, which provides a yield of the compound of formula (I) of not less than 95%.

15. Process according to claim 1, wherein R1 is hydrogen, R2 and R3 are independently methyl or ethyl, X and Y are chlorine, and n is zero.

16. Process according to claim 1, wherein the molar ratio in A is 1 to 2.

17. Process according to claim 1, wherein the alkali metal hydroxide is present in an at least about equimolar amount based on the amount of compounds (III).

18. Process according to claim 1, wherein the molar ratio of alkali metal hydroxide to compounds (III) is approximately 1.05 to 1.07.

19. Process according to claim 1 comprising initially charging as reaction medium an alkali metal hydroxide in a concentration of from 25% to 45% by weight.

20. Process according to claim 1 comprising initially charging as reaction medium an alkali metal hydroxide in a concentration of from 30% to 40% by weight.

* * * * *